United States Patent
Kato et al.

(10) Patent No.: US 10,550,052 B2
(45) Date of Patent: Feb. 4, 2020

(54) METHOD FOR SEPARATING AND PURIFYING ISOBUTYLENE AND METHOD FOR PRODUCING ISOBUTYLENE

(71) Applicant: Mitsubishi Chemical Corporation, Chiyoda-ku (JP)

(72) Inventors: Shimpei Kato, Chiyoda-ku (JP); Daisuke Tomikawa, Chiyoda-ku (JP); Manabu Hoshino, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/274,285

(22) Filed: Feb. 13, 2019

(65) Prior Publication Data

US 2019/0177250 A1  Jun. 13, 2019

Related U.S. Application Data

(63) Continuation of application No. PCT/JP2017/031815, filed on Sep. 4, 2017.

(30) Foreign Application Priority Data

Sep. 6, 2016  (JP) .................. 2016-173224

(51) Int. Cl.
  *C07C 1/24*  (2006.01)
  *C07C 7/11*  (2006.01)
  *C07C 7/04*  (2006.01)
  *C07C 11/09*  (2006.01)
  *C07C 7/148*  (2006.01)

(52) U.S. Cl.
  CPC .................. *C07C 7/11* (2013.01); *C07C 1/24* (2013.01); *C07C 7/04* (2013.01); *C07C 7/14891* (2013.01); *C07C 11/09* (2013.01)

(58) Field of Classification Search
  CPC ........... C07C 11/09; C07C 1/24; C07C 7/005; C07C 7/04; C07C 7/11; C07C 2521/12; C07C 7/14891; B01D 3/14; B01D 3/143; B01D 3/36; B01D 3/40; B01J 19/0046; B01J 19/245; B01J 2219/00006; B01J 2219/00277; B01J 2219/24
  See application file for complete search history.

(56) References Cited

U.S. PATENT DOCUMENTS 7,803,964 B2 * 9/2010 Tanaka .................... C07C 67/04
  560/205
9,169,183 B1 * 10/2015 Su ........................ C07C 41/09

2003/0009063 A1  1/2003 Yamase et al.
2009/0012327 A1  1/2009 Tanaka et al.
2017/0050896 A1  2/2017 Yasukawa et al.

FOREIGN PATENT DOCUMENTS

| JP | 4-247043 | 9/1992 |
|---|---|---|
| JP | 2003-2852 | 1/2003 |
| JP | 2013-506717 | 2/2013 |
| JP | 2013-516487 | 5/2013 |
| JP | 2013-522270 | 6/2013 |
| WO | WO2006/082965 A1 | 8/2006 |
| WO | WO2015/170686 A1 | 11/2015 |

OTHER PUBLICATIONS

International Search Report dated Nov. 7, 2017 in PCT/JP2017/031815 filed Sep. 4, 2017.
Written Opinion issued Nov. 7, 2017 in PCT/JP2017/031815 filed Sep. 4, 2017.
Vendelin Macho, et al., "Dehydration of $C_4$ alkanols conjugated with a positional and skeletal isomerization of the form $C_4$ alkenes", Applied Catlysis A: General, vol. 214, No. 2, 2001, 7 pages.
Joshua D. Taylor, et al., "Dehydration of Fermented Isobutanol for the Production of Renewable Chemicals and Fuels", Topics in Catalysis, vol. 53, No. 15-18, 2010, 9 pages.

* cited by examiner

Primary Examiner — Sharon Pregler
(74) Attorney, Agent, or Firm — Oblon, McClelland, Maier & Neustadt, L.L.P.

(57) ABSTRACT

Provided are an industrially advantageous method for separating and purifying isobutylene, the method enabling high-purity isobutylene to be efficiently obtained by a simple process, and a method for producing isobutylene. A method for separating and purifying isobutylene from a reaction gas containing the isobutylene and unreacted isobutanol, comprising:
  a step (1) of contacting the reaction gas containing the isobutylene and unreacted isobutanol with a first solvent to obtain a first gas containing the isobutylene and a recovered solution containing the unreacted isobutanol;
  a step (2) of contacting the first gas with a specific second solvent to allow the second solvent to absorb the isobutylene contained in the first gas to obtain an absorption solution containing the isobutylene; and
  a step (3) of distilling the absorption solution to obtain separated and purified isobutylene. A method for producing isobutylene using the separation and purification method.

8 Claims, 3 Drawing Sheets

METHOD FOR SEPARATING AND PURIFYING ISOBUTYLENE AND METHOD FOR PRODUCING ISOBUTYLENE

TECHNICAL FIELD

The present invention relates to a method for separating and purifying isobutylene prepared from isobutanol, and a method for producing isobutylene using the separation and purification method.

BACKGROUND ART

Most of conventional plastics are based on petroleum as the raw material thereof. In recent years, however, there is a concern regarding petroleum depletion, and $CO_2$ generated on combustion is a cause of global warming. Thus, chemicals derived from biomass, referred to as carbon neutral, have recently attracted attention as substitutes of petroleum. Meanwhile, a methacrylic resin, which is a type of plastics, has excellent characteristics such as transparency and weather resistance and thus has been used for various applications. As a raw material of such methacrylic resin, methyl methacrylate has been used. As a method for producing methacrolein or methacrylic acid, which is a raw material of the methyl methacrylate, the following method is known. In other words, there is a catalytic gas phase oxidation method which uses tert-butanol, methyl tert-butyl ether, or isobutylene as a raw material.

Various methods for producing a raw material to be used for production of methacrylic resin have been conventionally known. Patent Literatures 1 to 4 and Non Patent Literature 1 describe methods for synthesizing isobutylene from isobutanol.

PRIOR ART LITERATURE

Patent Literature

Patent Literature 1: JPH04-247043A
Patent Literature 2: JP2013-506717A
Patent Literature 3: JP2013-516487A
Patent Literature 4: JP2013-522270A

Non Patent Literature

Non Patent Literature 1: Topics in Catalysis (2010) 53, 1224-1230

SUMMARY OF THE INVENTION

Problems to be Solved by the Invention

These literatures describe methods for producing isobutylene by dehydrating isobutanol by use of a dehydration catalyst. Specifically, as the dehydration catalyst, Patent Literature 1 uses γ-alumina containing a specific amount of $SiO_2$, Patent Literatures 2 to 4 use γ-alumina, zeolite, and so on, and Non Patent Literature 1 uses γ-alumina.

In these literatures, however, methods for separating and purifying isobutylene and unreacted isobutanol and/or water produced, from a product containing isobutylene obtained by a dehydration reaction of isobutanol, have been insufficiently described.

Accordingly, it is the object of the present invention to provide an industrially advantageous method for separating and purifying isobutylene, the method enabling high-purity isobutylene to be efficiently obtained by a simple process, and a method for producing isobutylene using this separation and purification method.

Solutions to the Problems

[1] A method for separating and purifying isobutylene by separating and purifying the isobutylene from a reaction gas containing the isobutylene and unreacted isobutanol, the method comprising:
a step (1) of contacting the reaction gas containing the isobutylene and unreacted isobutanol with a first solvent to obtain a first gas containing the isobutylene and a recovered solution containing the unreacted isobutanol;
a step (2) of contacting the first gas with a second solvent selected from tert-butanol, a tert-butanol aqueous solution, and methyl tert-butyl ether to allow the second solvent to absorb the isobutylene contained in the first gas to obtain an absorption solution containing the isobutylene, and
a step (3) of distilling the absorption solution to obtain separated and purified isobutylene.

[2] The method for separating and purifying isobutylene according to [1], wherein the solvent used in the step (1) contains water.

[3] The method for separating and purifying isobutylene according to [1], comprising a step (4) of distilling the recovered solution containing the unreacted isobutanol obtained from the step (1) to obtain a distillate containing the unreacted isobutanol and a bottom product not substantially containing the unreacted isobutanol, wherein
at least a part of the bottom product is reused as at least a part of the first solvent in the step (1).

[4] The method for separating and purifying isobutylene according to [2], comprising a step (4) of distilling the recovered solution containing the unreacted isobutanol obtained from the step (1) to obtain a distillate containing the unreacted isobutanol and a bottom product not substantially containing the unreacted isobutanol, wherein
at least a part of the bottom product is reused as at least a part of the first solvent in the step (1).

[5] The method for separating and purifying isobutylene according to any one of [1] to [4], comprising a step (5) of hydrating the separated and purified isobutylene obtained from the step (3) to obtain tert-butanol, wherein
the tert-butanol obtained from the step (5) is used as the second solvent in the step (2).

[6] The method for separating and purifying isobutylene according to any one of [1] to [4], comprising a step (6) of reacting the separated and purified isobutylene obtained from the step (3) with methanol to obtain methyl tert-butyl ether, wherein
the methyl tert-butyl ether obtained from the step (6) is used as the second solvent in the step (2).

[7] A method for producing isobutylene from isobutanol, comprising:
a step (a) of subjecting isobutanol to a dehydration reaction to obtain a reaction gas containing isobutylene and unreacted isobutanol; and
a step (b) of separating and purifying the isobutylene from the reaction gas; wherein
the step (b) is carried out by the method for separating and purifying isobutylene according to any one of [1] to [6].

[8] The method for producing isobutylene according to [7], wherein the distillate containing the unreacted isobutanol, obtained in the method for separating and purifying isobutylene according to [3] or [4], is reused as isobutanol to be subjected to the step (a).

Effects of the Invention

According to the present invention, it is possible to provide an industrially advantageous method for separating and purifying isobutylene, the method enabling high-purity isobutylene to be efficiently obtained by a simple process, and a method for producing isobutylene using this separation and purification method.

MODE TO CARRY OUT THE INVENTION

The method for separating and purifying isobutylene of the present invention is suitably applicable to a reaction gas containing isobutylene prepared from isobutanol, particularly isobutanol derived from biomass. Additionally, according to the separation and purification method of the present invention, it is possible to continuously and efficiently obtain high-purity isobutylene from isobutanol.

Hereinbelow, the method for separating and purifying isobutylene and the method for producing isobutylene using the separation and purification method of the present invention will be described in detail. The explanation described below, however, is an exemplary embodiment of the present invention, and the present invention is not limited to the content thereof.

<Method for Separating and Purifying Isobutylene>

The method for separating and purifying isobutylene of the present invention is a method for separating and purifying isobutylene from a reaction gas containing the isobutylene and unreacted isobutanol. Accordingly, a reaction gas for use in this separation and purification method can be used without particular limitation as long as the gas contains isobutylene and unreacted isobutanol. As this reaction gas, for example, a reaction product (reaction gas) (including unreacted isobutanol) obtained by a reaction for synthesizing isobutylene from isobutanol (dehydration reaction) (described in Patent Literatures and the like mentioned above) can be used.

The method for separating and purifying isobutylene of the present invention has the following steps:
step (1): a step of contacting a reaction gas containing isobutylene and unreacted isobutanol with a first solvent to obtain a first gas containing the isobutylene and a recovered solution containing the unreacted isobutanol;
step (2): a step of contacting a second solvent selected from tert-butanol, a tert-butanol aqueous solution, and methyl tert-butyl ether with the first gas to allow the second solvent to absorb the isobutylene contained in the first gas to obtain an absorption solution containing the isobutylene; and step (3): a step of distilling the absorption solution to obtain separated and purified isobutylene.

The method for separating and purifying isobutylene of the present invention can also have the following steps:
step (4): a step of distilling the recovered solution containing the unreacted isobutanol obtained from the step (1) to obtain a distillate containing the unreacted isobutanol and a bottom product not substantially containing the unreacted isobutanol;
step (5): a step of hydrating the separated and purified isobutylene obtained from the step (3) to obtain tert-butanol; and
step (6): a step of reacting the separated and purified isobutylene obtained from the step (3) with methanol to obtain methyl tert-butyl ether.

In the present invention, the distillate obtained from the step (4) can be reused as isobutanol to be used when isobutylene is produced, and, at this time, it is possible to subject this distillate to a liquid-liquid separation step mentioned below. In other words, the separation and purification method of the present invention can also include this liquid-liquid separation step.

Each of these steps may be performed sequentially, or a plurality of the steps may be performed in parallel (simultaneously). Additionally, each of these steps can be performed a plurality of times. Sequentially repeating these steps many times can supply separated and purified isobutylene continuously.

Hereinbelow, each of the steps will be described in detail.
[Step (1)]

First, a reaction gas containing isobutylene and unreacted isobutanol is contacted with a first solvent. This allows the unreacted isobutanol to dissolve in the first solvent to separate the unreacted isobutanol from the reaction gas, and the unreacted isobutanol is recovered. This contact operation affords a first gas containing at least the isobutylene and a recovered solution containing the unreacted isobutanol (isobutanol recovery step).

Note that, as this reaction gas, a reaction product (including unreacted isobutanol) to be obtained by a known method of synthesizing isobutylene from isobutanol can be appropriately used, as mentioned above. This reaction gas contains at least isobutylene and (unreacted) isobutanol, and additionally can contain other components that may be generated when isobutylene is synthesized from isobutanol. Examples of the other components include isobutane, normal butane, normal butene, 1-butene, trans-2-butene, and cis-2-butene. Note that, naturally, the content of isobutylene in the reaction gas is preferably as high as possible.

The first solvent for use in the step (1) is not particularly limited and can be appropriately selected and used as long as it can dissolve (unreacted) isobutanol and dose not dissolve isobutylene. Specific examples of the first solvent can include polar protic solvents, and examples of the polar protic solvent include methanol, ethanol, and water. As the first solvent, one type of solvent may be used singly or a plurality of solvents may be used in combination. Of these, the first solvent preferably contains water and is more preferably water, because of its ease of handling. When the first solvent is water, effluent treatment resulting from separation and purification of isobutylene is facilitated, and running and facility costs can be easily reduced.

The first gas obtained from the step (1) contains at least isobutylene and, in addition to this, can contain the other components mentioned above that may be generated in synthesizing isobutylene from isobutanol.

Note that unreacted isobutanol may be contained in the first gas, but from the viewpoint of reducing the load on recovery of isobutanol, the content of unreacted isobutanol in the first gas is preferably 10.0% by mass or less, more preferably 5.0% by mass or less.

The recovered solution obtained from the step (1) contains at least (unreacted) isobutanol and the solvent used for the first solvent (e.g., water) and, in addition to these, can contain the other components mentioned above that may be generated in synthesizing isobutylene from isobutanol. Note that isobutylene may be contained in the recovered solution, but from the viewpoint of increasing the amount of isobutylene to be produced, the content of isobutylene in the recovered solution is preferably 0.01% by mass or less, more preferably 0.001% by mass or less.

As an apparatus to be used when the above reaction gas is contacted with the first solvent, a recovery column can be used, for example.

Examples of the recovery column that can be used include plate columns and packing material columns (irregular packing material columns and regular packing material columns).

The plate column can have a plurality of horizontal trays (column plates) in the column. In the plate column, gas-liquid equilibrium is established in each space (stage) divided by the trays. Accordingly, in the plate column, components that are highly volatile or not soluble in the first solvent (gases such as isobutylene herein) move to stages in the upper part of the column, and components that are low volatile or soluble in the first solvent (unreacted isobutanol and the like herein) move to stages in the lower part of the column. As these trays, turbo grid trays, dual flow tray, and sieve trays can be used, for example.

A packing material column, which is a hollow column packed with packing material, performs gas-liquid contact on the surface of the packing material. Examples of irregular packing materials that can be used for this packing material column include Raschig rings and Pall rings. Examples of regular packing materials that can be used for the packing material column include trade name: Mellapak (manufactured by Sulzer) and trade name: MC PACK (manufactured by Matsui Machine Ltd.).

Note that, as the apparatus for use in the step (1), a regular packing material column is preferably used because the apparatus can be downsized.

The recovery column can have a structure in which a supply line for a gas (the above reaction gas) is placed in the lower part of the column and a supply line for a solvent (the above first solvent) is placed in the upper part of the column. As mentioned above, the first gas containing isobutylene moves to the upper part of the recovery column and the recovered solution containing the unreacted isobutanol moves to the lower part of the recovery column. Thus, the recovery column can have a discharge line to recover the first gas at the column top and a discharge line to recover the recovered solution at the column bottom.

The contact method between the reaction gas and the first solvent herein is not particularly limited. However, the contact method between the reaction gas and the first solvent is preferably counter-current contact because the concentration of the (unreacted) isobutanol as the solute contained in the column top gas in the recovery column can be more reduced.

The column top pressure when the reaction gas is contacted with the first solvent in the apparatus (recovery column) is not particularly limited. However, the column top pressure at this time (gauge pressure) is preferably 0 MPaG or more and 0.10 MPaG or less, more preferably 0 MPaG or more and 0.03 MPaG or less. With a column top pressure during contact of 0 MPaG or more, the necessity for introducing pressure reducing equipment becomes eliminated. With a column top pressure of 0.10 MPaG or less, condensation of isobutylene can be easily suppressed, and mixing of isobutylene into the recovered solution can be easily suppressed.

The column top temperature when the reaction gas is contacted with the first solvent is preferably 10° C. or more and 60° C. or less, more preferably 20° C. or more and 50° C. or less. With a column top temperature during contact of 10° C. or more, condensation of isobutylene can be easily suppressed, and mixing of isobutylene into the recovered solution can be easily suppressed. With a column top temperature during contact of 60° C. or less, the recovery ratio of isobutanol can be further improved. Additionally, with a column top temperature during contact of 20° C. or more, condensation of isobutylene can be still further easily suppressed, and mixing of isobutylene into the recovered solution can be more easily suppressed. With a column top temperature during contact of 50° C. or less, the recovery ratio of isobutanol can be still further improved.

As described above, the first gas containing at least isobutylene and the recovered solution containing the unreacted isobutanol can be obtained by the step (1).

[Step (2)]

Next, the first gas obtained from the step (1) is contacted with a second solvent. This contact allows the second solvent to absorb the isobutylene contained in the first gas to obtain an absorption solution containing the isobutylene (isobutylene absorption step).

In the present invention, a solvent selected from tert-butanol, a tert-butanol aqueous solution, and methyl tert-butyl ether, which are polar protic solvents, is used as the second solvent. There is a possibility that the second solvent is distilled into the distillate (including the separated and purified isobutylene) of the distillation column for use in the step (3) mentioned below. Accordingly, in the present invention, these solvents are used because such solvents have little influence in producing methyl methacrylate even if mixed in the distillate. One type of second solvent may be used singly or a plurality of second solvents may be used in combination. From the viewpoint of suppressing upsizing of the equipment, it is more preferable to use one type of second solvent singly.

Note that tert-butanol can be produced by a hydration reaction of the (separated and purified) isobutylene obtained from the step (3), in the step (5) mentioned below. Thus, this tert-butanol to be obtained from the step (5) can be used as at least a part of the second solvent (tert-butanol and tert-butanol aqueous solution).

Methyl tert-butyl ether can be produced by a reaction between the (separated and purified) isobutylene obtained from the step (3) and methanol, in the step (6) mentioned below. Thus, this methyl tert-butyl ether to be obtained from the step (6) can be used as at least a part of the second solvent.

As mentioned above, these solvents can be available by using the separated and purified isobutylene, and it is not necessary to prepare a new solvent. Also from this point, a solvent selected from tert-butanol, a tert-butanol aqueous solution, and methyl tert-butyl ether is preferably used as the second solvent. Of these, from the viewpoint of safe operation of the apparatus and the absorption efficiency of isobutylene, it is more preferable to use a solvent selected from a tert-butanol aqueous solution and methyl tert-butyl ether as the second solvent.

The above tert-butanol aqueous solution can be constituted of tert-butanol and water. When a tert-butanol aqueous solution is used as the second solvent, the concentration of tert-butanol in the aqueous solution can be appropriately set in consideration of the operation conditions of the apparatus (an absorption column mentioned below) for use in the step (2). However, the concentration of tert-butanol in the tert-butanol aqueous solution is preferably 80% by mass or more and 90% by mass or less, more preferably 85% by mass or more and 88% by mass or less. When the concentration of tert-butanol is set at 80% by mass or more, it is possible to further increase the concentration of isobutylene to be absorbed by the second solvent. When the concentration of tert-butanol is set at 90% by mass or less, it is possible to easily set the freezing point of the tert-butanol aqueous solution at a moderate temperature to facilitate stable operation of the apparatus. The higher the concentration of tert-butanol in the tert-butanol aqueous solution, the higher the absorption efficiency tends to be. On the other hand, the higher the concentration of tert-butanol, the higer the freezing point tends to be. Thus, from the viewpoint of stable operation of the apparatus, it is required to raise the temperature of the tert-butanol aqueous solution to be used, and as a result, the absorption efficiency tends to decrease. From this trade-off relation, the concentration of tert-butanol in the tert-butanol aqueous solution is more preferably 85% by mass or more and 88% by mass or less.

The absorption solution to be obtained from the step (2) contains at least isobutylene and the second solvent and, in addition to these, can contain the other components mentioned above that may be generated in synthesizing isobutylene from isobutanol. Note that, naturally, the content of isobutylene in the absorption solution is preferably as high as possible.

As an apparatus for use when the first gas is contacted with the second solvent, an absorption column can be used, for example.

Examples of the absorption column that can be used include plate columns, irregular packing material columns, and regular packing material columns. As the apparatus for use in step (2), a regular packing material column is preferably used because the apparatus can be downsized.

The structure of these columns can be a structure similar to that of the recovery column mentioned above. Accordingly, in the absorption column, components that are highly volatile or not soluble in the second solvent (gases other than isobutylene and the like herein) move to the upper part of the column, and components that are low volatile or soluble in the second solvent (isobutylene and the like herein) move to the lower part of the column. Thus, the absorption column can have a discharge line to recover the absorption solution containing isobutylene at the column bottom and can have a discharge line to recover other gases and the like at the column top.

Additionally, the absorption column can have a structure in which a supply line for the gas (the above first gas) is placed in the lower part of the column and a supply line for the solvent (the above second solvent) is placed in the upper part of the column. The other gases discharged from this column top may contain isobutylene, but the content thereof is preferably as low as possible. Examples of the other gases can include other components mentioned above that may be generated in synthesizing isobutylene from isobutanol.

The contact method between the first gas and the second solvent herein is not particularly limited. However, the contact method between the first gas and the second solvent is preferably counter-current contact because the concentration of isobutylene as the solute contained in the column top gas in the absorption column can be more reduced.

The column top pressure when the first gas is contacted with the second solvent in the apparatus (absorption column) is not particularly limited. However, the column top pressure (gauge pressure) during contact is preferably 0 MPaG or more and 0.05 MPaG or less. With a column top pressure during contact of 0 MPaG or more, the necessity for introducing pressure reducing equipment becomes eliminated. With a column top pressure of 0.05 MPaG or less, the necessity for introducing large equipment having high pressure resistance becomes eliminated.

The column top temperature when the first gas is contacted with the second solvent is preferably 0° C. or more and 40° C. or less, more preferably 5° C. or more and 15° C. or less. With a temperature during contact of 0° C. or more, an ordinary cooler can be easily used, and thus, the equipment cost can be further reduced. With a temperature during contact of 40° C. or less, the dissolved concentration of isobutylene in the solvent can be further increased. Additionally, with a column top temperature during contact of 5° C. or more, an ordinary cooler can be more easily used, and the apparatus cost can be still further reduced. With a column top temperature during contact of 15° C. or less, the dissolved concentration of isobutylene in the solvent is still further increased, and the amount of the solvent used can be still further reduced.

[Step (3)]

The absorption solution obtained from the step (2) is distilled to obtain separated and purified isobutylene (isobutylene concentration step).

Examples of the apparatus that can be used in the step (3) include plate columns, irregular packing material columns, and regular packing material columns. As the apparatus for use in step (3), a regular packing material column is preferably used because the apparatus can be downsized.

The structure of these columns can be a structure similar to that of the recovery column mentioned above. Accordingly, in these columns, highly volatile components (isobutylene herein) move to the upper part of the column, and low volatile components (second solvent and the like herein) move to the lower part of the column. Thus, the apparatus (distillation column) for use in the step (3) can have a discharge line to recover isobutylene (distillate material) at the column top and can have a discharge line to recover the second solvent and the like at the column bottom.

Furthermore, the apparatus for use in the step (3) can have a supply line to supply the above absorption solution at the intermediate part (middle stage part) of the column, for example. This absorption solution can be supplied in a vaporized state by means of a heater, for example, from the supply line into the column. The apparatus for use in the step (3) can be provided with a reflux valve to return (at least) a part of the distillate material from the apparatus into the column, in order to sufficiently cause gas-liquid contact. The distillate material discharged from the column top is liquefied by a condenser or the like. The part of the liquefied distillate is returned into the column as reflux, and the remainder can be extracted as (a distillate including) separated and purified isobutylene. It is also possible to heat liquid components present at the column bottom by a reboiler or the like as required to vaporize highly volatile components such as isobutylene again. Thereby, higher-purity liquid components (including less isobutylene) (a bottom product including the second solvent and the like) can be obtained. The content of isobutylene in the liquid components discharged (recovered) from the column bottom is preferably 0.001% by mass or less from the viewpoint of increasing the amount of isobutylene to be produced.

As a condition in distilling the absorption solution, the column top pressure (gauge pressure) is preferably 0.05 MPaG or more and 0.4 MPaG or less, more preferably 0.10 MPaG or more 0.25 MPaG or less. The column top temperature is preferably 5° C. or more and 30° C. or less, more preferably 10° C. or more and 20° C. or less.

With a column top pressure during distillation of 0.05 MPaG or more, the condensation temperature of isobutylene can be further lowered. With a column top pressure of 0.4 MPaG or less, the cost for keeping the column top pressure can be further reduced.

Furthermore, with a column top pressure during distillation of 0.10 MPaG or more, the condensation temperature of isobutylene can be still further lowered, a condensation operation using ordinary cooling water can be easily performed, and thus, the apparatus cost can be further reduced. With a column top pressure of 0.25 MPaG or less, the cost for keeping the column top pressure can be still further reduced.

With a column top temperature during distillation of 5° C. or more, a condensation operation using ordinary cooling water can be easily performed, and thus, the apparatus cost can be further reduced. With a column top temperature of 30° C. or less, the amount of the absorption solution to be used can be easily reduced.

When a tert-butanol aqueous solution is used as the second solvent used for the absorption solution, the reflux ratio (amount refluxed/amount distilled) in distilling the absorption solution is preferably 0.1 or more and 10.0 or less, more preferably 3.0 or more and 4.0 or less. With a reflux ratio of 0.1 or more, a high concentration of isobutylene can be easily obtained. With a reflux ratio of 10.0 or less, the quantity of heat required can be further suppressed. With a reflux ratio of 3.0 or more, a high concentration of isobutylene can be more easily obtained. With a reflux ratio of 4.0 or less, the quantity of heat required can be still further suppressed.

Note that the above amount refluxed means the amount of the distillate material to be returned into the column out of the distillate material discharged from the column top and that the above amount distilled means the amount of the (distillate including) separated and purified isobutylene to be recovered from the column top without being returned into the column. Note that, naturally, the content (purity) of isobutylene in the (distillate including) separated and purified isobutylene is preferably as high as possible.

The distillate containing this isobutylene can also contain other components (e.g., the other components mentioned above that may be generated in synthesizing isobutylene from the second solvent and isobutanol).

When methyl tert-butyl ether is used as the second solvent, the reflux ratio in distilling the absorption solution is preferably 0.1 or more and 20.0 or less, more preferably 8.0 or more and 12.0 or less. With a reflux ratio of 0.1 or more, a high concentration of isobutylene can be easily obtained. With a reflux ratio of 20.0 or less, the quantity of heat required can be further suppressed. With a reflux ratio of 8.0 or more, a high concentration of isobutylene can be more easily obtained. With a reflux ratio of 12.0 or less, the quantity of heat required can be still further suppressed.

[Step (4)]

The recovered solution containing the unreacted isobutanol obtained from the step (1) is distilled to obtain a distillate containing the unreacted isobutanol and a bottom product not substantially containing the unreacted isobutanol (isobutanol concentration step). Note that the bottom product not substantially containing the unreacted isobutanol means a bottom product containing or not containing isobutanol with the recovery ratio of the unreacted isobutanol in the recovered solution of the step (1) being within an acceptable range, when this bottom product is used as at least a part of the first solvent in the step (1). The acceptable recovery ratio of the unreacted isobutanol in the recovered solution of the step (1) can be 80% or more, for example. Note that the content of the unreacted isobutanol in the bottom product is preferably 1% by mass or less, more preferably 0.1% by mass or less.

The content of the first solvent used in the bottom product obtained is preferably 95% by mass or more from the viewpoint of the acceptable concentration for wastewater treatment, and more preferably 99% by mass or more from the viewpoint of increasing the recovery ratio of the unreacted isobutanol.

In the separation and purification method of the present invention, at least a part of the bottom product obtained in step (4) can be reused in the step (1) as at least a part of the first solvent. When this bottom product is reused as the first solvent, in the step (1), only the bottom product recovered may be used as the first solvent, or the recovered bottom product may be combined with another solvent (e.g., water) and then may be used as the first solvent.

Additionally, in the method for producing isobutylene of the present invention mentioned below, the distillate obtained from the step (4) can be reused (recycled) as isobutanol (a raw material in a dehydration reaction) to be subjected to the step (a) mentioned below. When this distillate is reused as a raw material in a dehydration reaction, in the step (a), only the distillate recovered may be used as this raw material, or the recovered distillate may be combined with a new raw material (isobutanol) and then may be used as a raw material in a dehydration reaction.

Accordingly, in the present invention, the amount of the first solvent and the raw material in the dehydration reaction to be used can be easily suppressed, and it can be found that the present invention is an excellent process, also from the viewpoint of the environment and costs.

Examples of the apparatus (distillation column) that can be used in the step (4) include plate columns, irregular packing material columns, and regular packing material columns. As the apparatus for use in the step (4), a regular packing material column is preferably used because the apparatus can be downsized.

The structure of these distillation columns can be a structure similar to that of the recovery column mentioned above. Accordingly, in these distillation column, highly volatile components (unreacted isobutanol herein) move to the upper part of the column, and low volatile components (first solvent and the like herein) move to the lower part of the column. Thus, the apparatus (distillation column) for use in the step (4) can have a discharge line to recover the unreacted isobutanol (distillate) at the column top and can have a discharge line to recover the first solvent and the like (bottom product) at the column bottom.

Furthermore, the apparatus for use in the step (4) can have a supply line to supply the above recovered solution at the intermediate part (middle stage part) of the column. This recovered solution can be supplied in a vaporized state by means of a heater, for example, from the supply line into the column. The apparatus for use in the step (4) can be provided with a reflux valve to return (at least) a part of the distillate material from the apparatus into the column, in order to sufficiently cause gas-liquid contact. The distillate material discharged from the column top is liquefied by a condenser or the like. A part of the liquefied distillate is returned into the column as reflux, and the remainder can be extracted as a distillate. It is also possible to heat liquid components present at the column bottom by a reboiler or the like as required to thereby vaporize highly volatile components such as isobutanol again. Thereby, a higher-purity bottom product (including less isobutanol) can be obtained.

The conditions during distillation in the step (4) are not particularly limited, and, for example, the following conditions are preferably used. That is, the column top pressure (gauge pressure) during distillation is preferably 0 MPaG or more from the viewpoint of suppressing the equipment cost for introducing pressure reducing equipment, and is preferably 0.1 MPaG or less from the viewpoint of suppressing the equipment cost for introducing large pressurizing equipment.

The reflux ratio (amount refluxed/amount distilled) during distillation is preferably 0.1 or more and 10.0 or less, more preferably 1.0 or more and 2.0 or less. With a reflux ratio of 0.1 or more, a high concentration of isobutanol as a distillate can be easily obtained. With a reflux ratio of 10.0 or less, the quantity of heat required can be further suppressed. With a reflux ratio of 1.0 or more, a high concentration of isobutanol as a distillate can be more easily obtained. With a reflux ratio of 2.0 or less, the quantity of heat required can be still further suppressed.

Note that the above amount refluxed means the amount of the distillate material to be returned into the column out of the distillate material discharged from the column top and that the above amount distilled means an amount of the distillate including unreacted isobutanol to be recovered from the column top without being returned into the column.

When water, for example, is used as the first solvent, water may be present in the distillate. This distillate can be left to stand to be separated into an organic phase containing isobutanol and an aqueous phase (liquid-liquid separation step). The standing time in this case is preferably 10 minutes or more and 60 minutes or less, more preferably 15 minutes or more and 40 minutes or less. Accordingly, when water is mixed in the distillate, only the organic phase obtained by standing and separation is preferably recycled as a raw material for the dehydration reaction in the step (a). Thereby, mixing of water into a dehydration reactor in which the dehydration reaction is performed can be further suppressed, and a high reaction ratio can be easily maintained in view of equilibrium.

The entire bottom product recovered may be recycled as the first solvent, and the proportion of recycling (recycle ratio) is preferably within the following range. That is, recycle ratio is preferably 20% by mass or more and 50% by mass or less, more preferably 30% by mass or more and 40% by mass or less, based on the total amount of the bottom product.

With a recycle ratio of 20% by mass or more, the amount to be discharged can be further reduced. With a recycle ratio of 50% by mass or less, condensation of propanol generated by a side reaction can be easily suppressed.

With a recycle ratio of 30% by mass or more, the amount to be discharged can be still further reduced. With a recycle ratio of 40% by mass or less, condensation of propanol generated by a side reaction can be more easily suppressed.

[Step (5)]

A hydration reaction is performed by adding water to the separated and purified isobutylene obtained from the step (3) to obtain tert-butanol. This tert-butanol obtained from the step (5) can be used as at least a part of the second solvent (tert-butanol and a tert-butanol aqueous solution) for use in the step (2). Thereby, the present invention can easily suppress the amount of tert-butanol to be used in the second solvent, and thus is excellent also from the viewpoint of the environment and costs.

The hydration reaction to isobutylene in the step (5) can be performed by a conventionally known method. From the viewpoint of ease of catalyst separation, the reaction is preferably performed particularly using a cation exchange resin. As the cation exchange resin, strongly acidic cation exchange resins are preferable from the viewpoint of the activity to the hydration reaction. As the strongly acidic cation exchange resin, porous resins are preferable. Examples of the porous strongly acidic cation exchange resin include Lewatit (trade name) manufactured by Bayer AG and AMBERLYST (trade name) manufactured by Rohm and Haas Company.

As the reactor for performing the hydration reaction, reactors of any type by which solid-liquid contact is enabled can be used, and the type thereof is not particularly limited. As the reactor for use in the hydration reaction of the step (5), one continuous-flow-type fixed bed reactor or a plurality of such reactors arranged in series can be used, for example.

For example, when a reactor formed by arranging two fixed bed reactors (referred to as a first reactor and a second reactor) in series is used, the reaction temperature for both the fixed bed reactors is preferably set as follows. That is, from the viewpoint of suppressing an isobutylene dimer by a dimerization reaction of isobutylene, the reaction temperature of each reactor is preferably set at 65° C. or less. The above reaction temperature herein refers to the temperature at a part having the highest temperature in each reactor.

The (reaction) conversion ratio of isobutylene in the first reactor is preferably 50% or more. With a conversion ratio of isobutylene of 50% or more, the amount of isobutylene dimers to be by-produced in the second reactor or later can be easily suppressed. The reaction pressure in each reactor is not particularly limited, but a pressure at which the isobutylene or isobutylene-containing hydrocarbon and water assume a liquid state at the reaction temperature is employed. This reaction pressure is usually 0.2 to 5 MPaG.

[Step (6)]

Methanol is added to the separated and purified isobutylene obtained from the step (3) and reacted therewith to obtain methyl tert-butyl ether. The methyl tert-butyl ether obtained from the step (6) can be used for the second solvent used in the step (2). Thereby, the present invention can easily suppress the amount of a solvent to be used in the second solvent, and thus is excellent also from the viewpoint of the environment and costs.

The reaction of isobutylene with methanol in the step (6) can be performed by a conventionally known method. From the viewpoint of ease of catalyst separation, the reaction is preferably performed particularly using a cation exchange resin. As the cation exchange resin, strongly acidic cation exchange resins are preferable, from the viewpoint of the activity to the addition reaction of isobutylene with methanol. As the strongly acidic cation exchange resin, porous resins are preferable. As the porous strongly acidic cation exchange resin, the resins mentioned above in the step (5) can be used equally. As the reactor for performing the reaction of isobutylene with methanol, reactors of any type by which solid-liquid contact is enabled can be used, and the type is not particularly limited. As the reactor for use in the step (6), one continuous-flow-type fixed bed reactor or a plurality of such reactors arranged in series, or furthermore, a so-called reactive distillation column, in which a reaction zone is provided in a portion of a distillation column, or the like can be used, for example.

The reaction conditions in the step (6) can include the following conditions, for example. That is, the ratio of methanol to be supplied is 0.6 or more and 1.6 or less in a molar ratio (moles of methanol/moles of isobutylene) to isobutylene, and the reaction temperature is set at 20° C. or more and 100° C. or less. The reaction pressure is not particularly limited and can be appropriately set. For example, a pressure at which the isobutylene or isobutylene-containing hydrocarbon and methanol assume a liquid state at the reaction temperature is employed, and this reaction pressure is usually 0.2 to 5 MPaG.

<Method for Producing Isobutylene>

The method for producing isobutylene of the present invention, which is a method for producing isobutylene from isobutanol, has the following steps:

step (a): a step of subjecting isobutanol to a dehydration reaction to obtain a reaction gas containing isobutylene and unreacted isobutanol; and step (b): step of separating and purifying the isobutylene from the reaction gas.

Herein, in the production method of the present invention, the above step (b) is performed by using the method for separating and purifying isobutylene of the present invention mentioned above. The description of this separation and purification step will be omitted, because the detailed description thereof is already provided above.

[Step (a)]

Isobutanol is subjected to a dehydration reaction to obtain a reaction gas containing isobutylene and unreacted isobutanol (isobutanol dehydration step). For the dehydration reaction of isobutanol herein, conventionally known processes (e.g., the methods described in Patent Literatures mentioned above) can be appropriately used. As the dehydration catalyst to be used in the dehydration reaction, an acid catalyst can be used to perform the reaction, for example. Specific examples of the acid catalyst can include alumina, silica alumina, solid phosphoric acid, titania, and zirconia. One type of these acid catalysts may be used, or two or more types of these may be used in combination. Of these, from the viewpoint of the dehydration reaction activity of isobutanol, an alumina catalyst is preferably used.

The dehydration reaction of isobutanol is an endothermic reaction, and the reaction temperature is preferably controlled at 108° C. or more and 500° C. or less. The lower limit of the reaction temperature is more preferably 115° C. or more, even more preferably 150° C. or more. Meanwhile, the upper limit of the reaction temperature is more preferably 415° C. or less, even more preferably 400° C. or less.

When the dehydration reaction is performed in the step (a), a dehydration reactor can be used. Such a dehydration reactor is only required to have a structure in which a dehydration catalyst is present therein and can be in contact with isobutanol. Examples of the dehydration reactor that can be used include fixed bed reactors, and jacketed multi-tubular heat exchanger-type fixed bed reactors that have a system enabling a heat medium to circulate. Of these, multitubular heat exchanger-type fixed bed reactors that enable the reaction temperature to be easily controlled are preferable.

The pressure (gauge pressure) of the dehydration reactor is preferably 0 MPaG or more, more preferably 0.02 MPaG or more because a reaction gas can be easily supplied to the step (b) without provision of additional equipment. The pressure of the dehydration reactor is preferably 0.10 MPaG or less, more preferably 0.05 MPaG or less because a reduction in the conversion ratio due to an increase in the pressure can be more suppressed and the amount of the catalyst can be easily reduced.

EXAMPLES

The present invention will be described hereinbelow with reference to examples, but the present invention is not limited to these examples. Parts described in examples represent a flow rate based on the mass per unit time. A flow diagram illustrating an operation performed in each example is shown in each of FIGS. 1 to 5.

Example 1

A fixed bed reactor was packed with commercially available silica alumina (trade name: SA6175-3.0M, manufactured by Saint-Gobain) as a dehydration catalyst and maintained at 340° C. and 0 kPaG. Then, 100 parts of a gas of 100% by volume of isobutanol (raw material) (sign 100 in FIG. 1) was supplied to the fixed bed reactor at a space velocity of 3.0 $h^{-1}$ to contact the isobutanol with the silica alumina, and a reaction gas (sign 101 in FIG. 1) containing at least unreacted isobutanol and isobutylene was obtained (step (a): sign 10 in FIG. 1).

Subsequently, by use of an isobutanol recovery column that had five theoretical stages and of which column top pressure was maintained at 0 kPaG, the reaction gas (sign 101) was supplied to the fifth stage from the column top to be countercurrently contacted with 66.6 parts of a first solvent (water) of which temperature was controlled at 10° C. Then, the unreacted isobutanol was recovered from the reaction gas to the first solvent (water) side, and a first gas containing isobutylene (sign 121 in FIG. 1) and a recovered solution containing the unreacted isobutanol (sign 111 in FIG. 1) were obtained (step (1): sign 11 in FIG. 1).

To the third stage from the column top of an eight-theoretical stage distillation column having a column bottom temperature maintained at 100° C. and a column top pressure maintained at 0 kPaG, 91.7 parts of the isobutanol recovered solution obtained was supplied. With a reflux ratio set at 1.0, the recovered solution was separated by distillation (step (4): sign 12 in FIG. 1) into a distillate containing unreacted isobutanol (sign 125 in FIG. 1) and a bottom product not substantially containing unreacted isobutanol (sign 122 in FIG. 1). Subsequently, 3.3 parts of the distillate obtained was separated into an organic phase containing isobutanol and an aqueous phase using a decanter (liquid-liquid separation step: sign 13 in FIG. 1). Then, the organic phase obtained (recycled isobutanol (sign 132 in FIG. 1)) was recycled to the fixed bed reactor for use in the above step (a). The decanter at this time was maintained at 74.2° C. The aqueous phase in the decanter was treated as effluent (sign 131 in FIG. 1). Meanwhile, 29.6 parts out of 88.3 parts of the bottom product obtained was recycled as the first solvent (water) of the isobutanol recovery column for use in the step (1). The remaining bottom product was treated as effluent (sign 124 in FIG. 1). The first solvent (sign 112 in FIG. 1) other than the bottom product recycled (first solvent) (sign 123 in FIG. 1) was supplied separately.

Subsequently, by use of a 25-theoretical stage isobutylene absorption column having a column top pressure maintained at 0 kPaG, the first gas containing at least isobutylene (sign 121) obtained from the fixed bed reactor was supplied to the 25th stage from the column top to be countercurrently contacted with 840 parts of a second solvent (sign 142 in FIG. 1) of which temperature was controlled at 10° C. As the second solvent, used was a tert-butanol aqueous solution having a concentration of tert-butanol of 86.5% by mass. Thereby, isobutylene from the first gas was absorbed to the second solvent (tert-butanol aqueous solution) side (step (2): sign 14 in FIG. 1).

The isobutylene absorption solution obtained (sign 141 in FIG. 1), after the pressure thereof was raised to 250 kPaG using a pump, was supplied to the third stage from the column top of a 10-theoretical stage distillation column having a column bottom temperature maintained at 108.6° C. and a column top pressure maintained at 150 kPaG. Then, in this distillation column, with a reflux ratio set at 3.0, the absorption solution was separated by distillation into a distillate containing isobutylene (sign 151 in FIG. 1) and a bottom product containing the second solvent (tert-butanol aqueous solution) (sign 152 in FIG. 1) (step (3): sign 15 in FIG. 1). The amount of the distillate containing the separated and purified isobutylene obtained (product) was 75.5 parts, and the amount of the bottom product containing the tert-butanol aqueous solution was 106.3 parts. As a result, 72.2 parts of isobutylene as the target substance was produced, and the content of isobutylene in the distillate obtained was 95.6% by mass. Meanwhile, the content (concentration) of tert-butanol in the distillate was 0.005% by mass. However, as mentioned above, this tert-butanol is a solvent having little influence on production of a methacrylic resin. The amount of the effluent (the total amount of signs 124 and 131 in FIG. 1) was 60.7 parts.

Example 2

Figure 1:
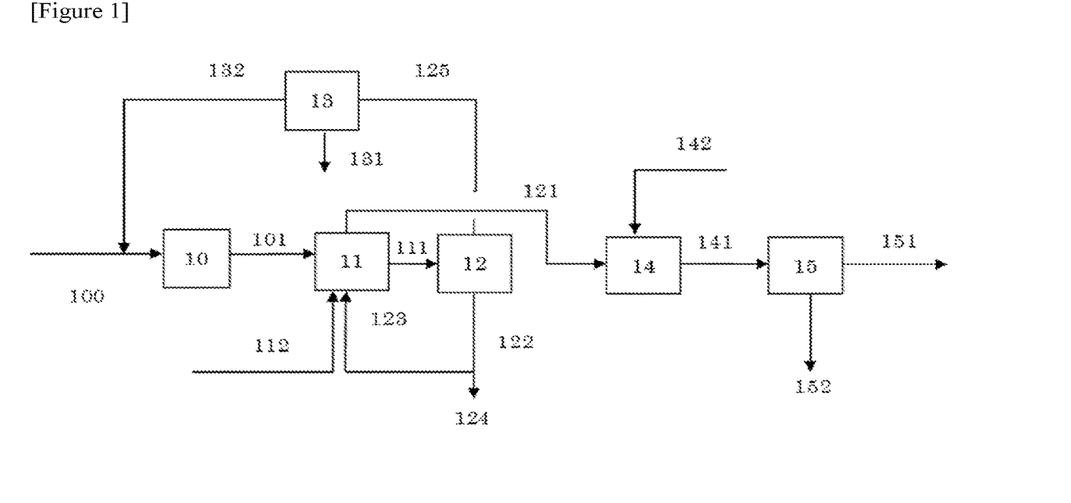
FIG. 1 is a flow diagram illustrating an operation performed in Example 1 and Example 5.
Figure 2:
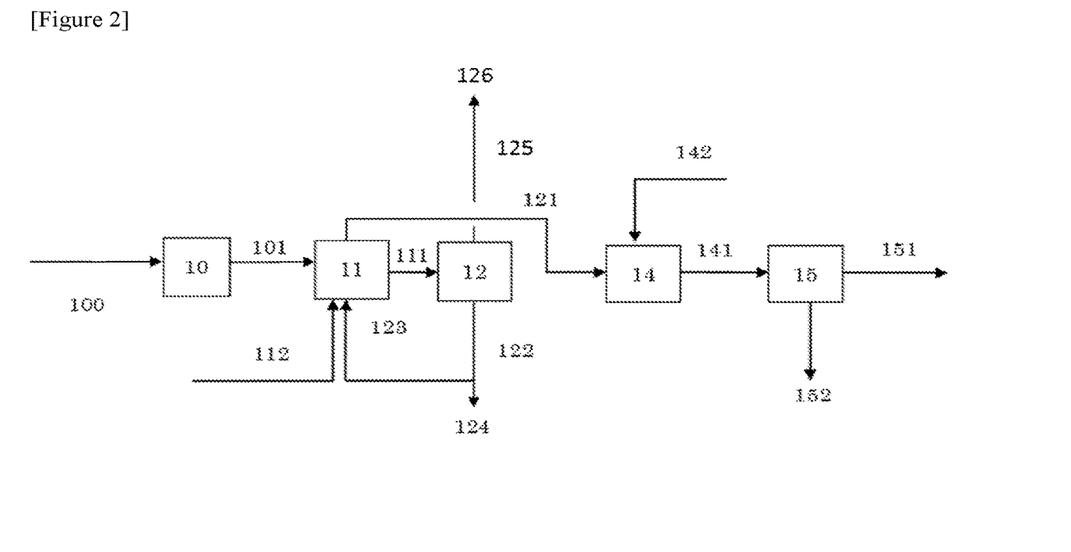
FIG. 2 is a flow diagram illustrating an operation performed in Example 2.

The amount of the distillate was 3.1 parts and the amount of the bottom product was 88.0 parts, obtained from the step (4) (sign 12 in FIG. 2). This distillate (sign 125 in FIG. 2) was treated as effluent (sign 126 in FIG. 2), and unreacted isobutanol was not recycled. In the same manner as in Example 1 except for those, a reaction gas containing isobutylene was synthesized from isobutanol and the reaction gas was separated and purified.

The amount of the distillate containing isobutylene (sign 151 in FIG. 2) was 74.2 parts and the amount of the bottom product containing the second solvent (tert-butanol aqueous solution) (sign 152 in FIG. 2) was 104.7 parts, obtained from the step (3) (sign 15 in FIG. 2). As a result, 71.1 parts of isobutylene as the target substance was produced, and the content of isobutylene in the distillate obtained (product) was 95.8% by mass. Meanwhile, the content (concentration) of tert-butanol in the distillate was 0.005% by mass. The amount of the effluent (the total amount of signs 124 and 126 in FIG. 2) was 60.1 parts.

Example 3

Figure 3:
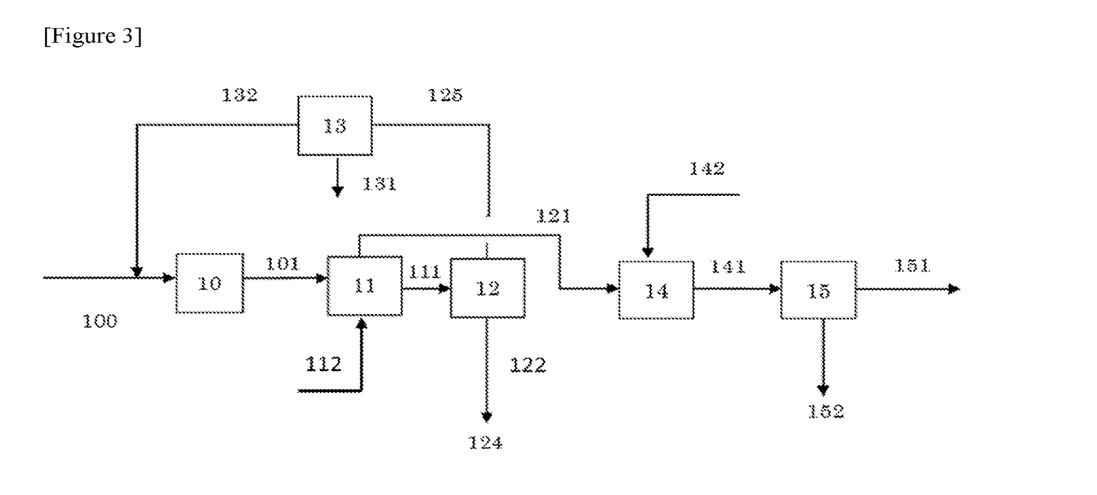
FIG. 3 is a flow diagram illustrating an operation performed in Example 3.

The amount of the distillate was 2.6 parts and the amount of the bottom product was 89.1 parts, obtained from the step (4) (sign 12 in FIG. 3). This bottom product (sign 122 in FIG. 3) was treated as effluent (sign 124 in FIG. 3), and the first solvent was not recycled. In the same manner as in Example 1 except for those, a reaction gas containing isobutylene was synthesized from isobutanol and the reaction gas was separated and purified.

The amount of the distillate containing isobutylene (sign 151 in FIG. 3) was 75.5 parts and the amount of the bottom product containing the second solvent (tert-butanol aqueous solution) (sign 152 in FIG. 3) was 106.3 parts, obtained from the step (3) (sign 15 in FIG. 3). As a result, 72.2 parts of isobutylene as the target substance was produced, and the content of isobutylene in the distillate obtained (product) was 95.6% by mass. Meanwhile, the content (concentration) of tert-butanol in the distillate was 0.005% by mass. The amount of the effluent (the total amount of signs 124 and 131 in FIG. 3) was 90.3 parts.

Example 4

A reaction gas containing isobutylene was synthesized from isobutanol and the reaction gas was separated and purified in the same manner as in Example 1 except that the followings were changed. That is, the amount of the isobutanol recovered solution obtained from the step (1) (sign 11 in FIG. 4) was 91.2 parts. This recovered solution (sign 111 in FIG. 4) was treated as effluent (sign 113 in FIG. 4), and unreacted isobutanol and the first solvent were not recycled.

Figure 4:
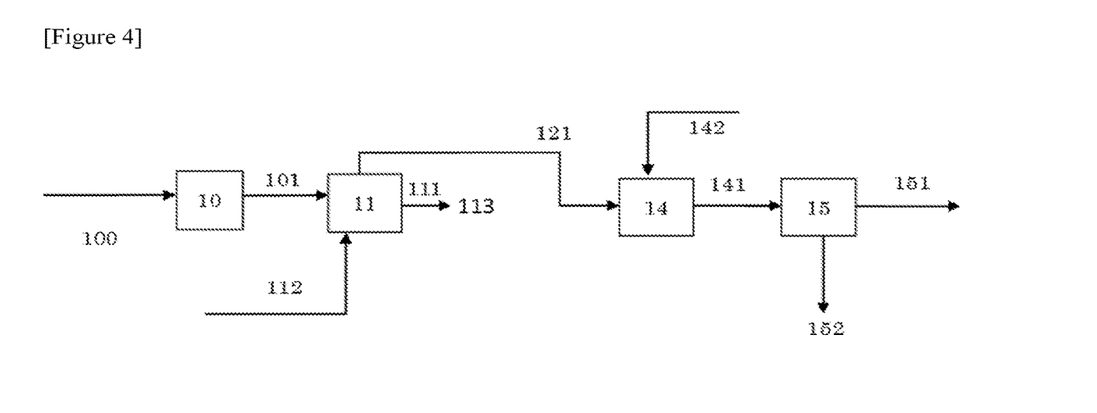
FIG. 4 is a flow diagram illustrating an operation performed in Example 4.
Figure 5:
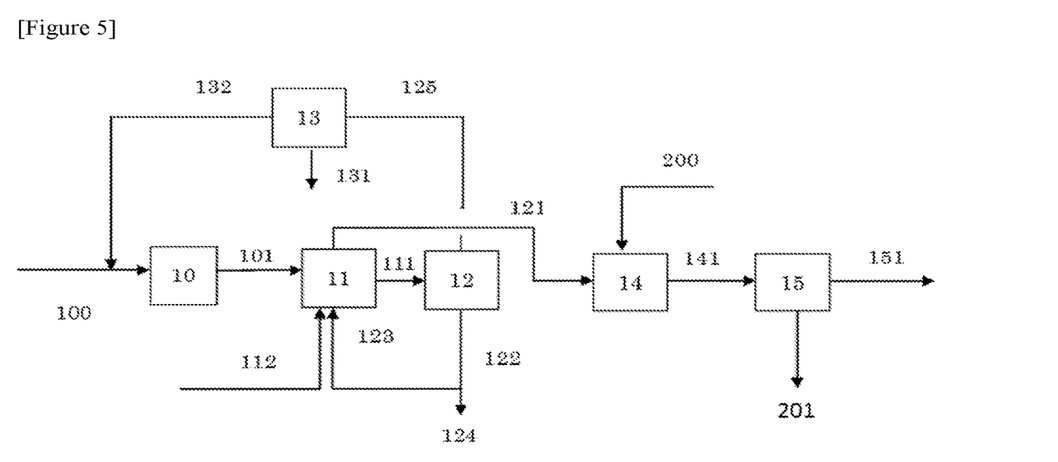
FIG. 5 is a flow diagram illustrating an operation performed in Comparative Example 1.

The amount of the distillate containing isobutylene (sign 151 in FIG. 4) was 74.2 parts and the amount of the bottom product containing the second solvent (tert-butanol aqueous solution) (sign 152 in FIG. 4) was 104.7 parts, obtained from the step (3) (sign 15 in FIG. 4). As a result, 71.1 parts of isobutylene as the target substance was produced, and the content of isobutylene in the distillate obtained (product) was 95.8% by mass. Meanwhile, the content (concentration) of tert-butanol in the distillate was 0.005% by mass. The amount of the effluent (sign 113 in FIG. 4) was 91.2 parts.

Example 5

A reaction gas containing isobutylene was synthesized from isobutanol and the reaction gas was separated and purified in the same manner as in Example 1 except that the followings were changed. That is, the second solvent (sign 142 in FIG. 1) used in the step (2) (sign 14 in FIG. 1) was replaced by 593 parts of 98.8% by mass (the purity of methyl tert-butyl ether) methyl tert-butyl ether of which temperature was controlled at 10° C. The column bottom temperature and the reflux ratio of the distillation column used in the step (3) (sign 15 in FIG. 1) were changed respectively to 88.9° C. and 9.7.

The amount of the distillate containing isobutylene (sign 151 in FIG. 1) was 79 parts and the amount of the bottom product containing the second solvent (methyl tert-butyl ether) (sign 152 in FIG. 1) was 122.7 parts, obtained from the step (3). As a result, 72.0 parts of isobutylene as the target substance was produced, and the content of isobutylene in the distillate obtained (product) was 91.1% by mass. Meanwhile, the content (concentration) of methyl tert-butyl ether in the distillate was 5.0% by mass. However, as mentioned above, this methyl tert-butyl ether is a solvent having little influence on production of a methacrylic resin. The amount of the effluent (the total amount of signs 124 and 131 in FIG. 1) was 60.7 parts.

Comparative Example 1

The second solvent used in the step (2) (sign 14 in FIG. 5) was replaced by 507 parts of n-hexane (sign 200 in FIG. 5) of which temperature was controlled at 10° C. And by the step (3) (sign 15 in FIG. 5), a distillate containing isobutylene (sign 151 in FIG. 5) and a bottom product containing n-hexane (sign 201 in FIG. 5) were obtained. In the same manner as in Example 1 except for those, a reaction gas containing isobutylene was synthesized from isobutanol and the reaction gas was separated and purified. The amount of the distillate containing isobutylene obtained was 112.9 parts, and the amount of the bottom product containing n-hexane obtained was 106.3 parts. As a result, 72.3 parts of isobutylene as the target substance was produced, and the content of isobutylene in the distillate obtained (product) was 64.0% by mass. Meanwhile, the content (concentration) of n-hexane in the distillate was 33.0% by mass. The amount of the effluent (the total amount of signs 124 and 131 in FIG. 5) was 60.7 parts.

Whether unreacted isobutanol was recycled or not, whether the first solvent was recycled or not, the amount of isobutylene produced that was finally obtained, the total amount of effluent, and the content of the second solvent or n-hexane in the product (distillate) of each example are shown in the following Table 1. When a tert-butanol aqueous solution was used as the second solvent herein, the second solvent contained in this product represents tert-butanol.

TABLE 1

| | Recycling of unreacted isobutanol | Recycling of first solvent | Amount of isobutylene produced | Total amount of effluent | Content of second solvent or n-hexane in product |
|---|---|---|---|---|---|
| Example 1 | Yes | Yes | 72.2 parts | 60.7 parts | 0.005% by mass |
| Example 2 | No | Yes | 71.1 parts | 60.1 parts | 0.005% by mass |
| Example 3 | Yes | No | 72.2 parts | 90.3 parts | 0.005% by mass |
| Example 4 | No | No | 71.1 parts | 91.2 parts | 0.005% by mass |
| Example 5 | Yes | Yes | 72.0 parts | 60.7 parts | 5.0% by mass |
| Comparative Example 1 | Yes | Yes | 72.3 parts | 60.7 parts | 33.0% by mass |

[Evaluation]

In Comparative Example 1, n-hexane was used as the second solvent in the step (2). Thus, n-hexane of 33.0% by mass were mixed in the product (distillate obtained from the step (3)), and it was not possible to obtain a high concentration of isobutylene. Furthermore, Example 1, in which the bottom product obtained from the step (4) was recycled as the first solvent and the distillate obtained from the step (4) was recycled as the raw material in the dehydration reaction, was compared with Example 4, in which the bottom product and the distillate were not recycled, to obtain the following results. That is, the amount of isobutylene produced, as the target substance, increased by 1.5% by mass (1.1 parts) and the effluent decreased by 33.4% by mass (30.5 parts) in Example 1 in comparison with those in Example 4.

REFERENCE SIGNS LIST

10: step (a)
11: step (1)
12: step (4)
13: liquid-liquid separation step
14: step (2)
15: step (3)
100: (raw material) isobutanol
101: reaction gas
111: recovered solution
112: first solvent
113, 124, 126, 131: effluent
121: first gas
122: bottom product
123: recycled bottom product (first solvent)
125: distillate
132: recycled isobutanol
141: absorption solution
142: second solvent
151: distillate containing isobutylene
152: bottom product containing second solvent
200: n-hexane
201: bottom product containing n-hexane

The invention claimed is:

1. A method for separating and purifying isobutylene by separating and purifying the isobutylene from a reaction gas containing the isobutylene and unreacted isobutanol, the method comprising:

a step (1) of contacting the reaction gas containing the isobutylene and unreacted isobutanol with a first solvent to obtain a first gas containing the isobutylene and a recovered solution containing the unreacted isobutanol;

a step (2) of contacting the first gas with a second solvent selected from tert-butanol, a tert-butanol aqueous solution, and methyl tert-butyl ether to allow the second solvent to absorb the isobutylene contained in the first gas to obtain an absorption solution containing the isobutylene, and a step (3) of distilling the absorption solution to obtain separated and purified isobutylene.

2. The method for separating and purifying isobutylene according to claim 1, wherein the first solvent used in the step (1) contains water.

3. The method for separating and purifying isobutylene according to claim 1, comprising a step (4) of distilling the recovered solution containing the unreacted isobutanol obtained from the step (1) to obtain a distillate containing the unreacted isobutanol and a bottom product not substantially containing the unreacted isobutanol, wherein at least a part of the bottom product is reused as at least a part of the first solvent in the step (1).

4. The method for separating and purifying isobutylene according to claim 2, comprising a step (4) of distilling the recovered solution containing the unreacted isobutanol obtained from the step (1) to obtain a distillate containing the unreacted isobutanol and a bottom product not substantially containing the unreacted isobutanol, wherein at least a part of the bottom product is reused as at least a part of the first solvent in the step (1).

5. The method for separating and purifying isobutylene according to any one of claims 1 to 4, comprising a step (5) of hydrating the separated and purified isobutylene obtained from the step (3) to obtain tert-butanol, wherein the tert-butanol obtained from the step (5) is used as the second solvent in the step (2).

6. The method for separating and purifying isobutylene according to any one of claims 1 to 4, comprising a step (6) of reacting the separated and purified isobutylene obtained from the step (3) with methanol to obtain methyl tert-butyl ether, wherein the methyl tert-butyl ether obtained from the step (6) is used as the second solvent in the step (2).

7. A method for producing isobutylene from isobutanol, comprising:
   a step (a) of subjecting isobutanol to a dehydration reaction to obtain a reaction gas containing isobutylene and unreacted isobutanol; and
   a step (b) of separating and purifying the isobutylene from the reaction gas; wherein
   the step (b) is carried out by the method for separating and purifying isobutylene according to any one of claims 1 to 6.

8. The method for producing isobutylene according to claim 7, wherein the distillate containing the unreacted isobutanol, obtained in the method for separating and purifying isobutylene according to claim 3 or 4, is reused as isobutanol to be subjected to the step (a).

* * * * *